United States Patent
Okuda et al.

(10) Patent No.: US 8,709,409 B2
(45) Date of Patent: Apr. 29, 2014

(54) METHOD FOR TREATING RHEUMATOID ARTHRITIS BY ADMINISTERING AN ANTI-IL-6 ANTIBODY AND METHOTREXATE

(75) Inventors: Osamu Okuda, Tokyo (JP); Noriaki Yoshida, Tokyo (JP); Revinder Nath Maini, Barnes (GB)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 55 days.

(21) Appl. No.: 12/382,160

(22) Filed: Mar. 10, 2009

(65) Prior Publication Data

US 2009/0181029 A1 Jul. 16, 2009

Related U.S. Application Data

(62) Division of application No. 10/554,407, filed as application No. PCT/JP2004/006211 on Apr. 28, 2004, now Pat. No. 7,521,052.

(30) Foreign Application Priority Data

Apr. 28, 2003 (GB) .................................. 0309619.5

(51) Int. Cl.
*A61K 39/395* (2006.01)
(52) U.S. Cl.
USPC .................. 424/130.1; 424/141.1; 424/145.1
(58) Field of Classification Search
None
See application file for complete search history.

(56) References Cited

U.S. PATENT DOCUMENTS

| | | |
|---|---|---|
| 5,126,250 A | 6/1992 | McDonough et al. |
| 5,171,840 A | 12/1992 | Kishimoto |
| 5,210,075 A | 5/1993 | Scholz et al. |
| 5,216,128 A | 6/1993 | Novick et al. |
| 5,480,796 A | 1/1996 | Kishimoto |
| 5,530,101 A | 6/1996 | Queen et al. |
| 5,670,373 A | 9/1997 | Kishimoto |
| 5,795,965 A | 8/1998 | Tsuchiya et al. |
| 5,817,790 A | 10/1998 | Tsuchiya et al. |
| 5,851,793 A | 12/1998 | Kishimoto |
| 5,888,510 A | 3/1999 | Kishimoto et al. |
| 5,990,282 A | 11/1999 | Kishimoto |
| 5,994,511 A | 11/1999 | Lowman et al. |
| 6,086,874 A | 7/2000 | Yoshida et al. |
| 6,261,560 B1 | 7/2001 | Tsujinaka et al. |
| 6,270,766 B1 | 8/2001 | Feldman et al. |
| 6,401,691 B1 | 6/2002 | Kawano et al. |
| 6,406,909 B1 | 6/2002 | Shibuya et al. |
| 6,410,691 B1 | 6/2002 | Kishimoto |
| 6,428,979 B1 | 8/2002 | Kishimoto |
| 6,537,782 B1 | 3/2003 | Shibuya et al. |
| 6,692,742 B1 | 2/2004 | Nakamura et al. |
| 6,723,319 B1 | 4/2004 | Ito et al. |
| 6,875,432 B2 | 4/2005 | Liu et al. |
| 6,962,812 B2 | 11/2005 | Shibuya et al. |
| 7,015,218 B1 * | 3/2006 | Ushio et al. ................. 514/227.8 |
| 7,320,792 B2 | 1/2008 | Ito et al. |
| 7,332,289 B2 | 2/2008 | Takeda et al. |
| 7,479,543 B2 | 1/2009 | Tsuchiya et al. |
| 7,498,031 B2 | 3/2009 | Fujioka et al. |
| 7,521,052 B2 | 4/2009 | Okuda et al. |
| 7,566,453 B2 | 7/2009 | Nakamura et al. |
| 7,666,413 B2 | 2/2010 | Liu et al. |
| 7,771,723 B2 | 8/2010 | Nakamura et al. |
| 7,824,674 B2 | 11/2010 | Ito et al. |
| 7,927,815 B2 | 4/2011 | Takeda et al. |
| 7,955,598 B2 | 6/2011 | Yoshizaki et al. |
| 8,017,121 B2 | 9/2011 | Kishimoto et al. |
| 8,142,776 B2 | 3/2012 | Liu et al. |
| 8,173,126 B2 | 5/2012 | Yoshizaki et al. |
| 8,227,195 B2 | 7/2012 | Stubenrauch et al. |
| 8,398,980 B2 | 3/2013 | Kano et al. |
| 8,420,789 B2 | 4/2013 | Takeda et al. |
| 8,440,196 B1 | 5/2013 | Funakoshi et al. |
| 8,470,316 B2 | 6/2013 | Yasunami |
| 2002/0045571 A1 | 4/2002 | Liu et al. |
| 2003/0190316 A1 | 10/2003 | Kakuta et al. |
| 2004/0115197 A1 | 6/2004 | Yoshizaki et al. |
| 2005/0118163 A1 | 6/2005 | Mizushima et al. |
| 2005/0175603 A1 | 8/2005 | Liu et al. |
| 2005/0214278 A1 | 9/2005 | Kakuta et al. |
| 2005/0238644 A1 | 10/2005 | Mihara et al. |
| 2006/0127975 A1 | 6/2006 | Link et al. |
| 2006/0134113 A1 | 6/2006 | Mihara |
| 2006/0142549 A1 | 6/2006 | Takeda et al. |
| 2006/0165696 A1 | 7/2006 | Okano et al. |
| 2006/0292147 A1 | 12/2006 | Yoshizaki et al. |
| 2007/0036785 A1 | 2/2007 | Kishimoto et al. |
| 2007/0098714 A1 | 5/2007 | Nishimoto et al. |
| 2007/0116700 A1 | 5/2007 | Liu et al. |
| 2007/0134242 A1 | 6/2007 | Nishimoto et al. |
| 2008/0124325 A1 | 5/2008 | Ito et al. |
| 2008/0124761 A1 | 5/2008 | Goto et al. |

(Continued)

FOREIGN PATENT DOCUMENTS

| | | |
|---|---|---|
| EP | 312996 | * 4/1989 |
| EP | 0 628 639 | 12/1994 |

(Continued)

OTHER PUBLICATIONS

Chuntharapai et al (1997) Method on Enzymology, vol. 288, pp. 15-27.*

(Continued)

*Primary Examiner* — Prema Mertz
(74) *Attorney, Agent, or Firm* — Foley & Lardner LLP

(57) ABSTRACT

A pharmaceutical composition for the treatment of interleukin-6 (IL-6) related diseases, comprising an interleukin-6 antagonist (IL-6 antagonist) and immunosuppressants. The IL-6 antagonist is preferably an antibody to an interleukin-6 receptor (IL-6R).

7 Claims, No Drawings

(56) References Cited

U.S. PATENT DOCUMENTS

| | | |
|---|---|---|
| 2008/0274106 A1 | 11/2008 | Nishimoto et al. |
| 2008/0306247 A1 | 12/2008 | Mizushima et al. |
| 2009/0022719 A1 | 1/2009 | Mihara et al. |
| 2009/0061466 A1 | 3/2009 | Hoesel et al. |
| 2009/0131639 A1 | 5/2009 | Kakuta et al. |
| 2009/0181029 A1 | 7/2009 | Okuda et al. |
| 2009/0220499 A1 | 9/2009 | Yasunami |
| 2009/0220500 A1 | 9/2009 | Kobara |
| 2009/0263384 A1 | 10/2009 | Okada et al. |
| 2009/0269335 A1 | 10/2009 | Nakashima et al. |
| 2009/0291076 A1 | 11/2009 | Morichika et al. |
| 2010/0008907 A1 | 1/2010 | Nishimoto et al. |
| 2010/0034811 A1 | 2/2010 | Ishida |
| 2010/0061986 A1 | 3/2010 | Takahaski et al. |
| 2010/0129355 A1 | 5/2010 | Ohguro et al. |
| 2010/0247523 A1 | 9/2010 | Kano et al. |
| 2010/0255007 A1 | 10/2010 | Mihara et al. |
| 2010/0285011 A1 | 11/2010 | Morichika et al. |
| 2010/0304400 A1 | 12/2010 | Stubenrauch et al. |
| 2011/0117087 A1 | 5/2011 | Franze et al. |
| 2011/0150869 A1 | 6/2011 | Mitsunaga et al. |
| 2011/0206664 A1 | 8/2011 | Yoshizaki et al. |
| 2011/0245473 A1 | 10/2011 | Igawa et al. |
| 2011/0262462 A1 | 10/2011 | Platt et al. |
| 2011/0268734 A1 | 11/2011 | Ito et al. |
| 2012/0009177 A1 | 1/2012 | Platt et al. |
| 2012/0064086 A1 | 3/2012 | Liu et al. |
| 2012/0076783 A1 | 3/2012 | Liu et al. |
| 2012/0183539 A1 | 7/2012 | Maeda |
| 2012/0219974 A1 | 8/2012 | Stubenrauch et al. |
| 2012/0301460 A1 | 11/2012 | Bao et al. |

FOREIGN PATENT DOCUMENTS

| | | |
|---|---|---|
| EP | 0 800 829 A1 | 10/1997 |
| EP | 0 923 941 A2 | 6/1999 |
| EP | 0 983 767 A1 | 3/2000 |
| EP | 1 074 268 A1 | 2/2001 |
| FR | 2 694 767 | 2/1994 |
| JP | 05-227970 A | 9/1993 |
| JP | 06-319396 A | 11/1994 |
| JP | 3630453 B | 3/1995 |
| JP | 7-188056 A | 7/1995 |
| JP | 08-099902 | 4/1996 |
| JP | 2002-510211 A | 4/2002 |
| JP | 2002-525104 A | 8/2002 |
| JP | 3822137 B2 | 11/2003 |
| JP | 2009-092508 A | 4/2009 |
| RU | 2195960 C2 | 1/2003 |
| WO | WO 97/10338 | 3/1997 |
| WO | WO 98/42377 A1 | 10/1998 |
| WO | WO 99/64070 | 12/1999 |
| WO | WO-00/0300 A3 | 1/2000 |
| WO | WO-00/03000 A2 | 1/2000 |
| WO | WO-00/10607-AI | 3/2000 |
| WO | WO 00/18804 A1 | 4/2000 |
| WO | WO 00/72864 A1 | 12/2000 |
| WO | WO-2002/13859 A1 | 2/2002 |
| WO | WO 2004/039826 A1 | 5/2004 |
| WO | WO-2005/089802 A1 | 9/2005 |
| WO | WO 2005/090405 A1 | 9/2005 |
| WO | WO-2008/016134 A1 | 2/2008 |
| WO | WO-2008/078715 A1 | 7/2008 |
| WO | WO-2011/013786 A1 | 2/2011 |
| WO | WO-2011/149046 A1 | 12/2011 |
| WO | WO-2011/149051 A1 | 12/2011 |
| WO | WO-2012/064627 A2 | 5/2012 |
| WO | WO-2012/064627 A3 | 5/2012 |
| WO | WO 2013/031237 A1 | 3/2013 |

OTHER PUBLICATIONS

Baert, Filip et al, "Influence of Immunogenicity on the Long-Term Efficacy of Infliximab in Crohn's Disease", New England Journal of Medicine, Feb. 2003, vol. 348, No. 7, pp. 601-608.

Choy, E. H. S. et al, "Therapeutic Benefit of Blocking Interleukin-6 Activity With an Anti-Interleukin-6 Receptor Monoclonal Antibody in Rheumatoid Arthritis: A Randomized, Double-Blind, Placebo-Controlled, Dose-Escalation Trial", Arthritis and Rheumatism, Dec. 2002, vol. 46, No. 12, pp. 3143-3150.

Ito, Hiroaki et al., "A Pilot Randomized Trial of a Human Anti-Interleukin-6 Receptor Monoclonal Antibody in Active Crohn's Disease", Gastroenterology, Apr. 2004, vol. 126,. No. 4, pp. 989-996.

Maini & Charisma Study Group, "A Double-Blind, Parallel Group, Controlled, Dose Ranging Study of the Safety, Tolerability, Phamacokinetics and Efficacy of Repeat Doses of MRA Given Alone or in Combination With Methotrexate in Patients With Rheumatoid Arthritis", Abstract of Presentation at Eular, Jun. 2003, 2 pages.

Maini, Ravinder et al., "Therapeutic Efficacy of Multple Intravenous Infusions of Anti-Tumor Necrosis Factor α Monoclonal Antibody Combined with Low-Dose Weekly Methotrexate in Rheumatoid Arthritis", Arthritis and Rheumatism, Sep. 1998, vol. 41, No. 9, pp. 1552-1563.

Nishimoto, N. et al., "Toxicity, Pharmacokinetics, and Dose-Finding Study of Repetitive Treatment with the Humanized Anti-Interleukin 6 Receptor Antibody MRA in Rheumatoid Arthritis. Phase I/II Clinical Study", Journal of Rheumatology, vol. 30, No. 7, Jul. 2003, pp. 1426-1435.

Nishimoto, Norihiro et al., "Safety and Efficacy of Repetitive Treatment with Humanized Anti-Interleukin-6 Receptor Antibody (MRA) in Rheumatoid Arthritis", Arthritis and Rheumatism, 2002, vol. 44, No. S9-191, p. S84, abstract only.

Nishimoto, Norihito et al, "The Long-term Safety and Efficacy of Humanized Anti-Interleukin-6 Receptor Monoclonal Antibody, MRA in Multicentric Castelman's Disease", Database Biosis Online Biosciences Information Service, Nov. 2003, 1 page.

Wagner, C. L., et al., "Consequences of Immunogenicity to the Therepeutic Monoclonal Antibodies ReoPre® and Remicade®", Immunogenicity of Therapeutic Biological Products, 2003, pp. 37-53.

Office Action issued on Nov. 20, 2009, in corresponding patent application in Colombia, 4 pages.

Cronstein et al., Eds., *Milestones in Drug Therapy: Methotrexate*, 2000, 71-75.

Office Action issued Jan. 11, 2011, in corresponding Japanese application 2006-507726, 4 pages.

Nishimoto, Norihiro, "Inflammation and cytokines—From pathophysiology to clinical application—A Therapy Targeting a Cytokine," Saishin Igaku, Apr. 10, 2002, 57(4):913-918, with English translation, 11 pages.

Yoshizaki, Kazuyuki, "Anti-cytokine therapy—Humanized anti-IL-6 receptor antibody therapy," Wako Workshop lecture overview, Nov. 9, 1999, 15:51-57, with English translation, 13 pages.

Office Action dated May 4, 2011, in corresponding Korean Application No. 10-2005-7020429.

Office Action dated May 4, 2011, in corresponding Korean Application No. 10-2009-7008629.

Aggarwal et al., "Methotrexate inhibits interleukin-6 production in patients with juvenile rheumatoid arthritis," Rheumatol. Int., 2003, 23:134-137.

Starnes, Jr., et al., "Anti-IL-6 monoclonal antibodies protect against lethal *Escherichia coli* infection and lethal tumor necrosis factor-α challenge in mice," Journal of Immunology, Dec. 15, 1990, 145(12):4185-4191.

Office Action dated Feb. 5, 2010, in corresponding EP 04 730 090.0, 4 pages.

Chugai Pharmaceutical Co., Ltd. "Late Phase II clinical trial results for MRA for rheumatoid arthritis," Press Release May 28, 2002, retrieved from the internet: http://www.chugai-pharm.co.jp/hc/ss/english/news/2002.html (retrieved on Feb. 1, 2010), 2 pages.

Chugai Pharmaceutical Co., Ltd. "Late Phase II clinical trial results for MRA for rheumatoid arthritis announced at 66th Annual Scientific Meeting of the American College of Rheumatology," Press Release Oct. 29, 2002, retrieved from the internet: http://www.chugai-pharm.co.jp/hc/ss/english/news/2002.html (retrieved on Feb. 1, 2010), 4 pages.

Main et al., "How does infliximab work in rheumatoid arthritis?" Arthritis Research, 2002, 4(Supp2):S22-S28.

(56) References Cited

OTHER PUBLICATIONS

Mihara et al., "Humanized Antibody to Human Interleukin-6 Receptor Inhibits the Development of Collagen Arthritis in Cynomolgul Monkeys," Clinical Immunology, Mar. 2001, 98(3):319-326.
Methotrexate sodium for injection label, Rev. 10/2003, 27 pages, (http://www.accessdata.fda.gov/drugsatfda_docs/label/2004/11719slr106_methotrexate_lbl.pdf).
Nishimoto et al., "The Long-Term Safety and Efficacy of Humanized Anti-Interleukin-6 Receptor Monoclonal Antibody, MRA in Multicentric Castleman's Disease," Blood, 2005, 102(11):646a-647a, Abstract 2389.
Weinblatt et al., "Adalimumab, a Fully Human Anti-Tumor Necrosis Factor α Monoclonal Antibody, for the Treatment of Rheumatoid Arthritis in Patients Taking Concomitant Methotrexate," Arthritis & Rheumatism, Jan. 2003, 48(1):35-45.
U.S. Appl. No. 08/414,425, filed Mar. 31, 1995, Kawano.
U.S. Appl. No. 09/762,550, filed Feb. 9, 2001, Funakoshi.
U.S. Appl. No. 13/722,919, filed Dec. 20, 2012, Kano.
U.S. Appl. No. 13/290,366, filed Nov. 7, 2011, Bao.
Harris, R.(1995). "Processing of C-terminal lysine and arginine residues of proteins isolated from mammalian cell culture." Journal of Chromatography A.705:129-134. ¶.
Hirano, T. et al. (Nov. 6, 1986)."Complementary DNA for a novel human interleukin (BSF-2) that induces B lymphocytes to produce immunoglobulin." Nature. 324:73-76.
Akira, S., et al., (1993). "Interleukin-6 in Biology and Medicine." Advances in Immunology. 54:1-78.
Lotz, M. et al. (Mar. 1, 1988) "B Cell Stimulating Factor 2/Interleukin 6 is a Costimulant for Human Thymocytes and T Lymphocytes." J. Exp. Med.:167:1253-1258.
Taga, T. et al. (Oct. 1, 1987)."Receptors for B Cell Stimulatory Factor 2: Quantitation, Specificity, Distribution, and Regulation of Their Expression." J. Exp. Med.:166:967-981.
Yamasaki, K. et al. (Aug. 12, 1988)."Cloning and Expression of the Human Interleukin-6 (BSF-2/IFN.beta. 2) Receptor." Science. 241:825-828.
Novick, D. et al. (Nov. 1, 1991). "Monoclonal Antibodies to the Soluble Human IL-6 Receptor: Affinity Purification, Elisa, and Inhibition of Ligand Binding." Hybridoma. 10:137-146.
Huang, Y, et al. (Nov. 5, 1993)."A Monoclonal Anti-Human IL-6 Receptor Antibody Inhibits the Proliferation of Human Myeloma Cells." Hybridoma. 12:621-630.
Sato, K. et al. (Feb. 15, 1993). "Reshaping a Human Antibody to Inhibit the Interleukin 6-dependent Tumor Cell Growth." Cancer Research.53:851-856.
Johnson, K. A. et al. (2007)."Cation exchange-HPLC and mass spectrometry reveal C-terminal amidation of an IgG1 heavy chain." Analytical Biochemistry.360:75-83.
"Guidance for Industry:Q6B Specifications: Test Procedures and Acceptance Criteria for Biotechnological/Biological Products," U.S. Department of Health and Human Services; Food and Drug Administration; Aug. 1999, retrieved on Sep. 3, 2009 from the internet: http://www.fda.gov/downloads/Drugs/GuidanceComplianceRegulatoryInformation-n/Guidances/ucm073488.pdf; Table of Contents, 24 pages.
Santora, L. C. (1999). "Characterization of Recombinant Human Monoclonal Tissue Necrosis Factor-α Antibody Using Cation-Exchange HPLC and Capillary Isoelectric Focusing," Analytical Biochemistry 275:98-108.
Lazar, A. C. (2004). "Matrix-assisted laser desorption/ionization mass spectrometry for the evaluation of the C-terminal lysine distribution of a recombinant monoclonal antibody," Rapid Communications in Mass Spectrometry 18:239-244.
Adamczyk, M. et al. (2002). "Complete Sequencing of Antivancomycin Fab Fragment by Liquid Chromatography-electrospray Ion Trap Mass Spectrometry with a Combination of Database Searching and Manual Interpretation of the MS/MS Spectra," Journal of Immunological Methods 260:235-249.

Hirata, Y. et al. (1989). "Characterization of IL-6 Receptor Expression by Monoclonal and Polyclonal Antibodies," The Journal of Immunology 143(9):2900-2906.
Merkler, D. J. et al. (1991). "Recombinant Type A Rat 75-kDa α-Amidating Enzyme Catalyzes the Conversion of Glycine-Extended Peptides to Peptide Amides via an α-Hydroxyglycine Intermediate," Archives of Biochemistry and Biophysics 289(1):192-196.
Miller, D. A. et al. (1992). "Characterization of a Bifunctional Peptidylglycine α-Amidating Enzyme Expressed in Chinese Hamster Ovary Cells," Archives of Biochemistry and Biophysics 298(2):380-388.
Ray, M. V. L. et al. (2002). "Production of Salmon Calcitonin by Direct Expression of a Glycine-extended Precursor in *Escherichia coli*," Protein Expression and Purification 26:249-259.
Antes, B. et al. (2007). "Analysis of Lysine Clipping of a Humanized Lewis-Y Specific IgG Antibody and Its Relation to Fc-Mediated Effector Function," Journal of Chromatography B, 852:250-256.
Clinicaltrials.Gov, (2005). "Phase III Comparative Study (Open-Label) of MRA for Rheumatoid Arthritis (RA)," Study Start Date Mar. 2003, Study first received on Sep. 2, 2005, Study Completion Date Feb. 2006, last updated Jan. 30, 2009, ClinicalTrials.gov Identifier: NCT00144508, Drug: MRA (Tocilizumab), with all results, last visited Sep. 19, 2012, 6 pages.
Clinicaltrials.Gov, (2005). "Comparative Study (Double-Blind) of MRA for Rheumatoid Arthritis (RA)," Study Start Date Feb. 2004, Study first received on Sep. 2, 2005, Study Completion Date, Apr. 2006, last updated Jan. 30, 2009, ClinicalTrials.gov Identifier: NCT00144521, Drug: MRA (Tocilizumab), with all results, last visited Sep. 19, 2012, 10 pages.
Clinicaltrials.Gov, (2005). "Study of MRA in Patients With Rheumatoid Arthritis (RA)," Study Start Date, Aug. 2001, Study first received on Sep. 2, 2005, Study Completion Date Jun. 2009, last updated Dec. 21, 2009, ClinicalTrials.gov Identifier: NCT00144651, Drug: MRA (Tocilizumab), with all results, last visited Sep. 19, 2012, 6 pages.
Johnson, K.A. et al. (2007, e-pub. Oct. 30, 2006). "Cation Exchange-HPLC and Mass-Spectrometry Reveal C-Terminal Amidation of an IgG1 Heavy Chain," Analytical Biochemistry 360:75-83.
Tassone et al., (2000). "Letter to the Editor: Synergistic induction of growth arrest and apoptosis of human myeloma cells by the IL-6 super-antagonist Sant7 and Dexamethasone," Cell Death and Differentiation, 7:327-328.
Hoenemann et al., (2001). "The IL-6 Receptor Antagonist Sant-7 Overcomes Bone Marrow Stormal Cell-Mediated Drug Resistance of Multiple Myeloma Cells," Int. J. Cancer, 93:674-680.
Clinical Hematology, (2000). 41(10):1093, 436.
Clinical Hematology, (1997). 38(4):281-284.
Sung et al., (2000). "Methotrexate suppresses the interleukin-6 induced generation of reactive oxyten species in the synoviocytes of rheumatoid arthritis," Immunopharmacology, 47:35-44.
Nishimoto et al., (2000). "Anti-interleukin 6 receptor antibody treatment in rheumatic disease," Ann. Rheum. Dis., 59(Suppl 1):i21-i27.
Hagihara et al., (2002). "A humanized anti-IL-6 receptor antibody (MRA) in RA therapy," Nippon Rinsho, 60(12):2401-2407, with English abstract on first page.
Giacomelli et al., (2002). "Combination therapy with cyclosporine and methotrexate in patients with early rheumatoid arthritis soon exhibits TNFα production without decreasing TNFα mRNA levels. An in vivo and in vitro study," Clinical and Experimental Rheumatology, 20:365-372.
Diagnostic Manual of Rheumatoid Arthritis (revised edition), Manual for Diagnosis and Treatment Guideline Based on EBM, Japan Rheumatism Foundation, Apr. 1, 2004, 92-93, with Partial English translation.
Nishimoto, Norihiro, "Anti-IL-6 Receptor Antibody 2, Effectiveness and Problems in Rheumatoid Arthritis," Therapeutics (Chiryo-Gaku), 2002, 36(12):1264-1267, with partial English translation.
U.S. Appl. No. 13/847,691, filed Mar. 20, 2013, Takeda et al.
Nishimoto, Norihiro et al., "Safety and Efficacy of Repetitive Treatment with Humanized Anti-Interleukin-6 Receptor Antibody (MRA) in Rheumatoid Arthritis", Arthritis and Rheumatism, 2001, vol. 44, No. S9-191, p. S84, abstract only.
The Merck Index [online] Fourteenth Edition, 2006, entry for Tocilizumab, one page, CAS No. 375823-41-9.

(56) References Cited

OTHER PUBLICATIONS

U.S. Prescribing Information for Actemra, www.gene.com/download/pdf/actemra_prescribing.pdf, revised Apr. 2013, initial U.S. Approval 2010, 36 pages.

Ishida et al., "The expression technology of chimeric and humanized antibodies," Nippon-rinsho, 2002, 60(3):439-444, with English abstract on first page.

* cited by examiner

METHOD FOR TREATING RHEUMATOID ARTHRITIS BY ADMINISTERING AN ANTI-IL-6 ANTIBODY AND METHOTREXATE

CROSS-REFERENCE TO RELATED APPLICATIONS

This application is a Divisional of U.S. application Ser. No. 10/554,407, which is the U.S. National Stage application of PCT/JP2004/006211, filed Apr. 28, 2004, which claims priority from United Kingdom application 0309619.5, filed Apr. 28, 2003. The entire contents of each of the aforementioned applications are incorporated herein by reference.

BACKGROUND OF INVENTION

1. Field of the Invention

The present invention relates to methods for the treatment of interleukin-6 (IL-6) related diseases by the combination of an interleukin-6 antagonist (IL-6 antagonist), particularly an antibody against interleukin-6 receptor (IL-6R) (anti-IL-6R antibody) with immunosuppressants and by administering the anti-IL-6R antibody at a high dose.

2. Related Art

IL-6 is a cytokine also termed B cell stimulating factor-2 (BSF2) or interferon β2. IL-6 was discovered as a differentiation factor involved in activation of B lymphocyte lineage cells (Hirano, T. et al., Nature, 324:73-76, 1986), and after then it has been demonstrated that IL-6 is the multifunctional cytokine which affects functions of various cells (Akira, S. et al., Adv. in Immunology, 54:1-78, 1993). It has been reported that IL-6 induces maturation of T lymphocyte lineage cells (Lotz, M. et al., J. Exp. Med., 167:1253-1258, 1988).

IL-6 transmits its biological activity via two types of protein on cells. One is IL-6 receptor which is a ligand binding protein with molecular weight of about 80 kD, to which IL-6 binds (Taga, T. et al., J. Exp. Med., 166:967-981, 1987; Yamasaki, K. et al., Science, 241:825-828, 1987). IL-6 receptor also occurs as soluble IL-6 receptor mainly composed of its extracellular region, in addition to a membrane binding type which penetrates through cell membrane and expresses on the cell membrane.

International publication WO 92/19759 describes various types of anti-IL-6R antibodies such as humanized anti-IL-6R antibodies and chimeric anti-IL-6R antibodies. WO 96/11020 describes the therapeutic agent for rheumatoid arthritis and the inhibitor of synovial cell growth of which primary ingredient is IL-6 antagonist such as anti-IL-6R antibody. WO 96/12503 describes the treatment of diseases attributed to IL-6 production, such as plasmacytosis, hyperimmunoglobulinemia, anemia, nephritis, cachexia, rheumatoid arthritis, Castleman's disease, and mesangial proliferative nephritis. WO 98/42377 describes protective/therapeutic agents of sensitized T cell related diseases such as multiple sclerosis, uveitis, chronic thyroiditis, delayed hypersensitivity, contact dermatitis and atopic dermatitis, of which active ingredient is anti-IL-6R antibody.

WO98/42377 describes the therapeutic agents of systemic erythematosus, of which active ingredient is anti-IL-6R antibody. WO99/47170 describes the therapeutic agents of Crohn's disease, of which active ingredient is anti-IL-6R antibody. WO00/10607 describes the therapeutic agents of pancreatitis, of which active ingredient is anti-IL-6R antibody. WO02/3492 describes the therapeutic agents of psoriasis, of which active ingredient is anti-IL-6R antibody. Additionally, WO02/080969 describes the therapeutic agents of juvenile idiopathic arthritis, of which active ingredient is anti-IL-6R antibody.

SUMMARY OF INVENTION

As described above, various preventive or therapeutic agents of which active ingredient is anti-IL-6R antibody have been known. However, it has not been known that synergistic effects can be obtained by the combination of anti-IL-6R antibody with immunosuppressants such as methotrexate (MTX) in the treatment of IL-6 related diseases, the immunosuppressant such as methotrexate (MTX) can reduce or prevent allergic reactions upon the treatment of rheumatoid arthritis with anti-IL-6R antibody, and that anti-IL-6R antibody at a high dose can reduce or prevent allergic reactions upon the treatment of rheumatoid arthritis with anti-IL-6R antibody.

Therefore, the present invention provides a pharmaceutical composition for the treatment of IL-6 related disease, comprising an interleukin-6 antagonist (IL-6 antagonist) and immunosuppressants.

The invention also provides a pharmaceutical composition comprising immunosuppressants, for the effect enhancement on the use of an IL-6 antagonist for the treatment of IL-6 related disease.

The invention also provides a pharmaceutical composition comprising immunosuppressants, for the prevention or reduction of allergic reactions upon the treatment of IL-6 related diseases with the IL-6 antagonist.

The invention further provides a therapeutic agent for IL-6 related diseases to administer at a high dose, comprising an IL-6 antagonist.

The invention further provides a pharmaceutical composition comprising an IL-6 antagonist at a high dose, for the prevention or reduction of allergic reactions upon the treatment of IL-6 related diseases.

The IL-6 antagonist is preferably an anti-IL-6R antibody. The anti-IL-6R antibody is preferably a monoclonal antibody against IL-6R. Preferably, the anti-IL-6R antibody is the monoclonal antibody against human IL-6R. Or, preferably, the anti-IL-6R antibody is the monoclonal antibody against mouse IL-6R. Preferably, the anti-IL-6R antibody is a recombinant type antibody. Preferably, the human anti-IL-6R monoclonal antibody is, for example, PM-1 antibody. Preferably, the mouse anti-IL-6R monoclonal antibody is, for example, MR16-1 antibody. The antibody may be further a chimeric antibody, a humanized antibody or a human antibody against IL-6R. Specific preferable anti-IL-6R antibody is, for example, humanized PM-1 antibody.

When combining the IL-6 antagonist, particularly the anti-IL-6R antibody with the immunosuppressant, the dosage of the IL-6 antagonist, particularly the anti-IL-6R antibody is, for example, in the case of intravenous infusion, from 0.02 to 150 mg/kg/4 weeks or the dosage showing an anti-IL-6R antibody concentration in blood equivalent thereto, preferably from 0.5 to 30 mg/kg/4 weeks or the dosage showing the anti-IL-6R antibody concentration in blood equivalent thereto, and more preferably from 2 to 8 mg/kg/4 weeks or the dosage showing the anti-IL-6R antibody concentration in blood equivalent thereto.

When administering the IL-6 antagonist, particularly the anti-IL-6R antibody at a high dose, the dosage of the IL-6 antagonist, particularly the anti-IL-6R antibody is, for example, in the case of intravenous infusion, not less than 4 mg/kg/4 weeks or the dosage showing the anti-IL-6R antibody concentration in blood equivalent thereto, preferably from 6 to 16 mg/kg/4 weeks or the dosage showing an anti-IL-6R antibody concentration in blood equivalent thereto, and more preferably from 6 to 10 mg/kg/4 weeks or the dosage showing the anti-IL-6R antibody concentration in blood equivalent thereto.

When MTX is used as the immunosuppressant, the dosage of MTX is, for example, from 1 to 100 mg/body/weeks or the dosage showing the MTX concentration in blood equivalent thereto, preferably from 4 to 50 mg/body/week or the dosage showing the MTX concentration in blood equivalent thereto, and particularly preferably from 10 to 25 mg/body/weeks or the dosage showing the MTX concentration in blood equivalent thereto.

The dosage showing the drug (e.g., anti-IL-6R antibody MTX) concentration in blood means a dosage giving an equivalent therapeutic effect, and even when the transition of the concentration in blood varies according to the administration method such as intravenous injection and subcutaneous injection, it is regarded as the dosage showing the drug (e.g., anti-IL-6R antibody or MTX) concentration in blood so long as the therapeutic effect is equivalent.

Examples of the IL-6 related diseases include,

Acute chronic inflammatory diseases and autoimmune diseases: nephritis, mesangial proliferative nephritis, Crohn's disease, ulcerative colitis, pancreatitis, juvenile idiopathic arthritis or systemic juvenile idiopathic arthritis, vasculitis, Kawasaki disease, rheumatoid arthritis, systemic erythematosus, psoriasis, Sjogren syndrome, adult Still's disease;

neoplasmic diseases: multiple myeloma, Castleman's disease, malignant lymphoma, renal cancer;

infectious diseases: infection with HIV, infection with EBV;

cachexia: cachexia others: plasmacytosis, hyperimmunoglobulinemia, anemia and so on, and are preferably rheumatoid arthritis, plasmacytosis, hyperimmunoglobulinemia, anemia, nephritis, cachexia, multiple myeloma, Castleman's disease, mesangial proliferative nephritis, systemic erythematosus, Crohn's disease, pancreatitis, psoriasis, juvenile idiopathic arthritis or systemic juvenile idiopathic arthritis.

The pharmaceutical composition of the invention can be administered orally or parenterally and systemically or topically. For instance, intravenous injection such as drip infusion, intramuscular injection, intraperitoneal injection, subcutaneous injection, suppository, colonic injection, oral enteric coating drug and the like can be selected, and the administration method can be appropriately selected depending on a age and condition of a patient. The upper and lower limits of the actual dosage are affected by the frequency of administration, for example, the dosage per dose increases in the case of long administration interval whereas it decreases in the case of short administration interval.

For the preferable dosage and administration method of the anti-IL-6 receptor antibody, for instance, the amount at an extent as the free antibody exists in blood is the effective dosage. As specific examples, there are methods to administer dividing one to several times, for example, according to an administration schedule of twice/week, once/week, once/two weeks, once/4 weeks, once/6 weeks, once/8 weeks and the like by the method of intravenous injection such as drip infusion and subcutaneous injection. The administration schedule can be adjusted such as extending the administration interval from twice/week or once/week to once/2 weeks, once/3 weeks, once/4 weeks, once/6 weeks and once/8 weeks with observing the disease condition and changes of laboratory data in blood.

When administered in combination with MTX, the dosage of the anti-IL-6R antibody is typically, for example, in the case of the rheumatoid arthritis treatment, the dosage more than 0.5 mg/kg per week or the dosage showing an equivalent or more anti-rheumatic effect. For instance, when the intravenous administration is carried out once four weeks, the dosage is from 0.02 to 150 mg/kg, preferably from 0.5 to 30 mg/kg, and more preferably from 2 to 8 mg/kg.

The anti-IL-6R antibody and the immunosuppressant are administered simultaneously or with a time interval.

The immunosuppressants also encompass anti-rheumatic agents, adrenocortical hormone agents and the like, and include, for example, the following drugs.

A. Immunosuppressants, Anti-Rheumatic Agents, Adrenocortical Hormone Agents Immunosuppressants Alkylating Agents
Cyclophosphamide
Metabolic Antagonists
Azathioprine, methotrexate, mizoribine
T Cell Activity Inhibitors
Cyclosporine, tacrolimus Anti-Rheumatic Agents:

Hydroxychloroquine, sulfasalazine, leflunomide, etanercept, infliximab, adalimumab, D-penicillamine, oral gold compound, injectable gold compound (intramuscular injection), minocycline, sodium gold thiomalate, auranofin, D-penicillamine, lobenzarit, bucillamine, actarit;

Adrenocortical Hormone Agents:

Cortisone, hydrocortisones
Cortisone acetate, hydrocortisone, hydrocortisone sodium phosphate, hydrocortisone sodium succinate, fludrocortisone acetate
Prednisolone, prednisolones
Prednisolone, prednisolone sodium succinate, prednisolone sodium phosphate, halopredone acetate
Methyl prednisolones
Methyl prednisolone, methyl prednisolone acetate, methyl prednisolone sodium succinate
Triamcinolones
Triamcinolone, triamcinolone acetate, triamcinolone actinide
Dexamethasones
Dexamethasone, dexamethasone acetate, dexamethasone sodium phosphate, dexamethasone palmitate
Betamethasones
Betamethasone (betamethasone sodium phosphate), betamethasone, betamethasone sodium phosphate
Paramethasones
Paramethasone acetate The dosage of the immunosuppressant is, for example when MTX is combined for the rheumatoid arthritis treatment, for example in the case of orally administering, from 1 to 100 mg/body per week, preferably from 4 to 50 mg, and more preferably from 7.5 to 25 mg/body.

Also, a high dosage of the anti-IL-6R antibody means the dosage capable of preventing or reducing the allergic reaction, which is equal to or more than a minimum dosage effective for the treatment of IL-6 related diseases. For instance, in the rheumatoid arthritis treatment, when intravenous drip fusion is administered every four weeks, the dosage includes 4 mg/kg or more, preferably from 6 to 16 mg/kg, and more preferably from 6 to 10 mg/kg.

The above administration method, interval, and dosage are exemplifications of preferable examples, and the administration method, interval, and dosage which show similar therapeutic effects can be appropriately selected. For instance, it is possible to select the administration method, interval, and dosage which show the similar effects to those of the above preferable examples by measuring the concentrations of various medicines in blood. The invention includes the administration method, interval, and dosage which achieve the equivalent concentrations in blood to those of the above examples.

MODE FOR CARRYING OUT THE INVENTION

The IL-6 antagonist used in the invention may be used without regard to its origin, type and form as long as it exhibits the preventive or therapeutic effect on IL-6 related diseases.

The IL-6 antagonists are substances which inhibit biological activity of IL-6. The IL-6 antagonists are preferably the substances having an inhibitory effect on the binding to either IL-6, IL-6R or gp130. The IL-6 antagonists include anti-IL-6 antibody, anti-IL-6R antibody, anti-gp130 antibody, modified IL-6, modified soluble IL-6R, or partial peptides of IL-6 or IL-6R, as well as low molecular substances which exhibit the similar activity thereto.

The anti-IL-6 antibody used in the invention can be obtained as polyclonal or monoclonal antibody using means known in the art. As the anti-IL-6 antibody used in the invention, the monoclonal antibody derived from mammalian animals is preferable. The monoclonal antibodies derived from mammalian animals include those in produced hybridomas, and those produced in host cells transformed with expression vector containing the antibody gene by gene engineering technique. This antibody inhibits the binding of IL-6 to IL-6 receptor by binding to IL-6 to block signaling of IL-6 biological activity into cells.

Such antibodies include MH166 (Matsuda, T. et al., Eur. J. Immunol., 18:951-956, 1988) and SK2 (Sato, K. et al., The 21st Proceedings of the Japanese Society for Immunology, 21:166, 1991).

Hybridomas producing the anti-IL-6 antibody can be made basically using the technology known in the art as follows. That is, the hybridomas can be made by performing immunization using IL-6 as a sensitized antigen according to the standard immunization method, fusing the resultant immunized cells to parent cells known in the art by the standard cell fusion method, and screening cells producing the monoclonal antibody by the standard screening method.

Specifically, the anti-IL-6 antibody can be made as follows. For instance, human IL-6 used as the sensitized antigen to obtain the antibody can be obtained using the genel amino acid sequence of IL-6 disclosed in Eur. J. Biochem., 168:543-550, 1987; J. Immunol., 140:1534-1541, 1988; or Agr. Biol. Chem., 54:2685-2688, 1990.

The gene sequence of IL-6 is inserted into the expression vector known in the art, which transforms appropriate host cells, subsequently, the target IL-6 protein is purified from the cells or the culture supernatant by the method known in the art, and the purified IL-6 protein can be used as the sensitized antigen. Also, the fusion protein of the IL-6 protein with the other protein may be used as the sensitized antigen.

The anti-IL-6 receptor antibody used in the invention can be obtained as polyclonal or monoclonal antibody using means known in the art. As the anti-IL-6 receptor antibody used in the invention, the monoclonal antibody derived from mammalian animals is preferable. The monoclonal antibodies derived from mammalian animals include those in produced hybridomas, and those produced in host cells transformed with expression vector containing the antibody gene by gene engineering technique. This antibody inhibits the binding of IL-6 to IL-6 receptor by binding to IL-6 receptor to block signaling of IL-6 biological activity into cells.

Such antibodies include MR16-1 antibody (Tamura, T. et al., Proc. Natl. Acad. Sci. USA, 90:11924-11928, 1993), PM-1 antibody (Hirata, Y. et al., J. Immunol., 143:2900-2906, 1989), AUK-12-20 antibody, AUK64-7 antibody or AUK146-15 antibody (International Patent Application Publication No. WO 92-19759). Among them, the particularly preferable antibody includes PM-1 antibody.

The hybridoma cell line producing PM-1 antibody as PM-1 has been internationally deposited at International Patent Organism Depository (AIST Tsukuba Central 6, 1-1, Higashi 1-chome, Tsukuba-shi, Ibaraki Pref.) on the basis of Budapest Treaty as FERM BP-2998 on Jul. 12, 1989. The hybridoma cell line producing MR16-1 antibody as rat-mouse hybridoma MR16-1 has been internationally deposited at International Patent Organism Depository (AIST Tsukuba Central 6, 1-1, Higashi 1-chome, Tsukuba-shi, Ibaraki Pref.) on the basis of Budapest Treaty as FERM BP-5875 on Mar. 13, 1997.

Hybridomas producing the anti-IL-6 receptor monoclonal antibody can be made basically using the technology known in the art as follows. That is, the hybridomas can be made by performing immunization using IL-6 receptor as a sensitized antigen according to the standard immunization method, fusing the resultant immunized cells to parent cells known in the art by the standard cell fusion method, and screening cells producing the monoclonal antibody by the standard screening method.

Specifically, the anti-IL-6 receptor antibody can be made as follows. For instance, human IL-6 receptors used as the sensitized antibody to obtain the antibody can be obtained by using IL-6 receptor gene/amino acid sequences disclosed in European Patent Application Publication No. EP325474 and JP-A-3-155795, respectively.

The IL-6 receptor protein has two types, i.e., one expressed on cells and one dissociated from the cell membrane (soluble IL-6 receptor) (Yasukawa, K. et al., J. Biochem., 108:673-676). The soluble IL-6 receptor is substantially composed of an extracellular region of the IL-6 receptor, and is different from the membrane binding IL-6 receptor in lacking a transmembrane region or transmembrane and intracellular regions. Both IL-6 receptor proteins may be used as long as they are used as the sensitized antigen for the production of the anti-IL-6 receptor antibody used in the invention.

The gene sequence of IL-6 receptor is inserted into the expression vector known in the art, which transforms appropriate host cells, subsequently, the target IL-6 receptor protein is purified from the cells or the culture supernatant by the method known in the art, and the purified IL-6 receptor protein can be used as the sensitized antigen. Also, the cells expressing IL-6 receptor and the fusion protein of the IL-6 receptor protein with the other protein may be used as the sensitized antigen.

*E. coli* containing plasmid, pIBIBSF2R including cDNA encoding human IL-6 receptor as HB101-pIBIBSF2R has been internationally deposited at International Patent Organism Depository (AIST Tsukuba Central 6, 1-1, Higashi 1-chome, Tsukuba-shi, Ibaraki Pref.) on the basis of Budapest Treaty as the access No. FERM BP-2232 as of Jan. 9, 1989.

The anti-gp130 antibody used in the invention can be obtained as polyclonal or monoclonal antibody using means known in the art. As the anti-gp130 antibody used in the invention, the monoclonal antibody derived from mammalian animals is preferable. The monoclonal antibodies derived from mammalian animals include those in produced hybridomas, and those produced in host cells transformed with expression vector containing the antibody gene by gene engineering technique. This antibody inhibits the binding of IL-6/IL-6 receptor complex to gp130 by binding to gp130 to block signaling of IL-6 biological activity into cells.

Such antibodies include AM64 antibody (JP-A-3-219894), 4B11 antibody and 2H4 antibody (U.S. Pat. No. 5,571,513), B-S12 antibody and B-P8 antibody (JP-A-8-291199).

Hybridomas producing the anti-gp130 monoclonal antibody can be made basically using the technology known in the art as follows. That is, the hybridomas can be made by performing immunization using gp130 as a sensitized antigen according to the standard immunization method, fusing the resultant immunized cells to parent cells known in the art by the standard cell fusion method, and screening cells producing the monoclonal antibody by the standard screening method.

Specifically, the monoclonal antibody can be made as follows. For instance, gp130 used as the sensitized antigen to obtain the antibody can be obtained by using the gp130 gene/amino acid sequences disclosed in European Patent Application Publication No. EP 411946.

The gene sequence of gp130 is inserted into the expression vector system known in the art, which transforms appropriate host cells, subsequently, the target gp130 protein is purified from the cells or the culture supernatant by the method known in the art, and the purified gp130 protein can be used as the sensitized antigen. Also, the cells expressing gp130 and the fusion protein of the gp130 protein with the other protein may be used as the sensitized antigen.

Mammalian animals immunized with the sensitized antigen are not particularly limited, but preferably selected in consideration of compatibility with parent cells used for cell fusion. In general, rodent animals such as mouse, rat and hamster are used.

Immunization of the animal with the sensitized antigen is carried out according to the methods known in the art. As the general methods, it is carried out by injecting the sensitized antigen to the animal intraperitoneally or subcutaneously. Specifically, it is preferred that the sensitized antigen is appropriately diluted and suspended with PBS (phosphate-buffered saline) or saline, which is mixed with an appropriate amount of standard adjuvant, e.g., Freund's complete adjuvant to be emulsified, and subsequently administered to the mammalian animal several times with an interval of 4 to 21 days. Also, an appropriate carrier can be used upon the immunization with the sensitized antigen.

The animal is immunized in this way and it is confirmed that levels of the desired antibody are increased in serum. Subsequently, the immunized cells are removed from the mammalian animal, and are committed for cell fusion. Preferable immunized cells committed for cell fusion particularly include spleen cells.

For myeloma cells of the mammalian animals as partner parent cells fused with the above immunized cells, cell lines already known in the art, e.g., P3X63Ag8.653 (Kearney, J. F. et al., J. Immunol., 123:1548-1550, 1979), P3X63Ag8U.1 (Current Topics in Microbiology and Immunology, 81:1-7, 1978), NS-1 (Kohler, G. and Milstein, C., Eur. J. Immunol., 6:511-519, 1976), MOC-11 (Margulies D. H. et al., Cell, 8:405-415, 1976), SP2/0 (Shulman, M. et al., Nature, 276: 269-270, 1978), FO (de St. Groth, S. F. et al., J. Immunol, Methods, 35:1-21, 1980), S194 (Trowbridge, I. S. J. Exp. Med., 148:311-323, 1978), R210 (Galfre, G. et al., Nature, 277:131-133, 1979) are appropriately used.

The cell fusion of the above immunized cells with myeloma cells can be carried out basically according to the methods known in the art, e.g., Milstein's method (Kohler G. and Milstein C., Methods Enzymol., 73:3-46, 1981).

More specifically, the above cell fusion is performed, for example, in the standard nutrient culture medium in the presence of a cell fusion accelerator. As the cell fusion accelerator, for example, polyethyleneglycol (PEG), Sendai virus (HVJ) and the like are used, and an auxiliary agent such as dimethylsulfoxide can be further added/used as desired in order to increase the fusion efficiency.

A use ratio of the immunized cells to the myeloma cells is preferably, for example, 1 to 10 folds of the immunized cells to the myeloma cells. As media used for the above cell fusion, the use of RPMI 1640 medium, MEM medium suitable for growth of the myeloma cell line, and the other standard media used for this type of cell culture is possible, and further serum supplement such as feral calf serum (FCS) can be combined.

For the cell fusion, the target fused cells (hybridomas) are formed by thoroughly mixing the above immunized cells with the myeloma cells at the given amounts in the above medium, adding PEG solution, e.g., PEG solution with average molecular weight of about 1000 to 6000 prewarmed at 37° C. at a standard concentration of 30 to 60% (w/v), and mixing. Subsequently, a cell fusion agent and the like which are not preferable for the growth of the hybridomas can be removed by repeating the manipulation of sequentially adding the appropriate medium and removing the supernatant by centrifuge.

The hybridomas are selected by culturing in the standard selection medium, e.g., HAT medium (medium containing hypoxanthine, aminopterin and thymidine). The culture in the HAT medium is continued for typically from several day to several weeks, sufficient time period until cells other than the target hybridomas (non-fused cells) die out. Then, the standard limiting dilution method is performed, and the hybridomas producing the target antibody are screened and cloned.

Also in addition to obtaining the above hybridoma by immunizing the animal other than human with the antigen, desired human antibody having binding activity to the desired antigen or cells expressing the antigen can be obtained by sensitizing human lymphocytes with the antigen protein or the cells expressing the antigen in vitro, and fusing the sensitized B lymphocytes with human myeloma cells, e.g., U266 (see JP-B-1-59878). Moreover, the antigen or antigen expressing cells may be administered to transgenic animals having repertoire of human antibody gene to obtain the desired human antibody according to the method described above (See International Patent Application Publication Nos. WO 93/12227, WO 92/03918, WO 94/02602, WO 94/25585, WO 96/34096, WO 96/33735).

The hybridoma producing the monoclonal antibody made in this way can be cultured in the standard culture medium, and also can be stored in liquid nitrogen for a long time.

In order to obtain the monoclonal antibody from the hybridomas, employed is the method where the hybridomas are cultured according to the standard method and the monoclonal antibody is obtained as its culture supernatant, or the method where the hybridomas are propagated by administering to the compatible mammalian animal therewith and the monoclonal antibody is obtained as its ascites. The former method is suitable for obtaining the antibody with a high purity, and the latter method is suitable for producing the antibody at a large scale.

For instance, the production of the hybridoma producing the anti-IL-6 receptor antibody can be carried out by the method disclosed in JP-A-3-139293. The method where hybridomas producing PM-1 antibody internationally deposited at International Patent Organism Depository (AIST Tsukuba Central 6, 1-1, Higashi 1-chome, Tsukuba-shi, Ibaraki Pref.) as FERM BP-2998 on Jul. 12, 1989 on the basis of Budapest Treaty are injected intraperitoneally to BALB/c mouse to obtain the ascites and PM-1 antibody is purified from this ascites can be carried out. Also, the method where the present hybridomas are cultured in the appropriate medium, for example, RPMI 1640 medium, hybridoma SFM medium (supplied from GIBCO-BRL), PFHM-II medium (supplied from GIBCO-BRL) containing 10% fetal calf serum and 5% BM-Condimed H1 (supplied from Boehringer Mannheim) and PM-1 antibody is purified from its culture supernatant can be carried out.

In the invention, as the monoclonal antibody, it is possible to use recombinant type antibody produced by cloning the antibody gene from the hybridoma, inserting the gene into an appropriate vector, introducing this into host cells, and using gene engineering technology (see, for example, Borrebaeck, C. A. K. and Larrick, J. M., Therapeutic Monoclonal Antibodies, published in the United Kingdom by Macmillan Publishers Ltd., 1990).

Specifically, mRNA encoding the variable (V) region of the antibody is isolated from the cells producing the target antibody, e.g., hybridomas. For the isolation of mRNA, total RNA is prepared by the methods known in the art, e.g., guanidine ultracentrifuge method (Chirgwin, J. M. et al., Biochemistry, 18:5294-5299, 1979), AGPC method (Chomczynski, P. et al., Anal. Biochem., 162:156-159, 1987), and mRNA is prepared by the use of mRNA Purification Kit (supplied from Pharmacia). Also, mRNA can be directly prepared by the use of QuickPrep mRNA Purification Kit (supplied from Pharmacia).

cDNA of the antibody V region is synthesized from the resultant mRNA using reverse transcriptase. The synthesis of cDNA can be carried out using AMV Reverse Transcriptase First-strand cDNA Synthesis Kit and the like. Also, 5'-Ampli FINDER RACE kit (supplied from Clontech) and 5'-RACE method using PCR (Frohman, M. A. et al., Proc. Natl. Acad. Sci. USA, 85:8998-9002, 1988; Belyavsky A. et al., Nucleic Acids Res., 17:2919-2932, 1989) can be used to synthesize and amplify cDNA. The target DNA fragment is purified from the resultant PCR product, and ligated to the vector DNA. Further, a recombinant vector is made by this, which is introduced into *E. coli*, and colonies are selected to prepare the desired recombinant vector. The base sequence of the target DNA is confirmed by the method known in the art, e.g., deoxy method.

If the DNA encoding the V region of the target antibody is obtained, this is ligated to DNA encoding the constant (C region) region of the desired antibody, and then it is incorporated into the expression vector. Or the DNA encoding the V region of the antibody may be incorporated into the expression vector containing the C region of the antibody.

In order to produce the antibody used in the invention, the antibody gene is incorporated into the expression vector so as to express under the expression regulation regions such as enhancer and promoter as described later. Next, host cells can be transformed with this expression vector to express the antibody.

In the invention, artificially modified gene recombinant antibodies, e.g., chimeric antibody, humanized antibody and human antibody can be used for the purpose of reducing allogenic antigenicity for human. These modified antibodies can be made using the known methods.

The chimeric antibody can be obtained by ligating the DNA encoding the antibody V region obtained as above to the DNA encoding the human antibody C region and incorporating this into expression vector to be introduced to host to produce (see European Patent Application Publication NO. EP 125023, International Patent Application Publication No. WO 92/19759). Using these known methods, the chimeric antibody useful for the invention can be obtained.

For example, the plasmids containing DNA encoding the V regions of the L and H chains of the PM-1 chimeric antibody were named pPM-k3 and pPM-h1, respectively, and *E. coli* having these plasmids have been internationally deposited at National Collections of Industrial, Food and Marine Bacteria Limited (23 St. Machar Drive, Aberdeen AB2 1RY, Scotland, United Kingdom) as NCIMB 40366 and NCIMB 40362, respectively on Feb. 12, 1991 on the basis of Budapest Treaty.

The humanized antibodies are also referred to as reshaped human antibodies, are those in which the complementarity determining region (CDR) of the antibody of the mammalian animal other than human, e.g., mouse is transplanted in the complementarity determining region of the human antibody, and its general gene recombinant method has been known (see European Patent Application Publication NO. EP 125023, International Patent Application Publication No. WO 92/19759).

Specifically, the DNA sequence designed to link the CDR of the mouse antibody to the framework region (FR) of the human antibody is synthesized by PCR from several oligonucleotides made to have an overlapping portion at the terminus. The resultant DNA is ligated to the DNA encoding the human antibody C region, then it is incorporated into the expression vector, which is introduced into the host to produce the humanized antibody (see European Patent Application Publication NO. EP 239400, International Patent Application Publication No. WO 92/19759).

As FR of the human antibody ligated via the CDR, those are selected where the complementarity determining region forms a good antigen binding site. Amino acids in the framework region of the antibody variable region may be substituted as needed such that the complementarity determining region of the reshaped human antibody forms the proper antigen binding site (Sato, K. et al., Cancer Res., 53:851-856, 1993).

The human antibody C region is used for the chimeric antibody and humanized antibody. The human antibody C region includes Cγ, and for example, Cγ1, Cγ2, Cγ3 or Cγ4 can be used. The human antibody C region may be modified to improve stability of the antibody or the production thereof.

The chimeric antibody is composed of the variable region of the antibody derived from the mammalian animal other than human and the C region derived from the human antibody. The humanized antibody is composed of the complementarity determining region the antibody derived from the mammalian animal other than human and the framework region and the C region derived from the human antibody. Therefore, these have reduced antigenicity in the human body and thus are useful as the antibody used in the invention.

Preferable specific examples of the humanized antibody used in the invention include humanized PM-1 antibody (see International Patent Application Publication No. WO 92-19759).

Also, as the methods to obtain the human antibody, the technology to obtain the human antibody by panning using human antibody library is known in addition to the methods described above. For example, the variable region of the human antibody can be expressed on the surface of phages as a single strand antibody (scFv) by the phage display method, and the phages bound to the antigen can be selected. When the gene of the selected phages is analyzed, the DNA sequence encoding the variable region of the human antibody bound to the antigen can be determined. If the DNA sequence of scFv bound to the antigen is demonstrated, the sequence can be made by an appropriate expression vector to obtain the human antibody. These methods have been already well-known, and it is possible to cite WO 92101047, WO 92/20791, WO 93/06213, WO 93/11236, WO 93/19172, WO 95/01438, and WO 95/15388.

The antibody gene constructed as described above can be expressed and obtained by the methods known in the art. In the case of the mammalian cells, the antibody gene can be expressed by the DNA in which commonly useful promoter, the antibody gene to be expressed, and poly A signal 3' downstream therefrom are functionally bound, or by the vector containing them. For instance, promoter/enhancer can include human cytomegalovirus immediate early promoter/enhancer.

Also, as the other promoter/enhancer capable of being used for the expression of the antibody used in the invention, the viral promoter/enhancer of retrovirus, polyoma virus, adenovirus, simian virus 40(SV40), and the promoter/enhancer derived from the mammalian cells human elongation factor 1α (HEF1α) can be used.

For instance, the expression can be performed according to Mulligan et al's method (Mulligan, R. C. et al., Nature, 277: 108-114, 1979) in the case of using SV40 promoter/enhancer, or Mizushima et al's method (Mizushima, S and Nagata, S., Nucleic Acids Res., 18:5322, 1990) in the case of using HEF1α promoter/enhancer.

In the case of *E. coli*, the gene can be expressed by functionally binding commonly useful promoter, a signal sequence for antigen secretion and the antibody gene to be expressed. For instance, the promoters can include lacZ promoter and araB promoter. Ward et al's method (Ward, E. S. et al., Nature, 341:544-546, 1989; Ward, E. S. et al., FASEB J., 6:2422-2427, 1992) and Better et al's method (Better, M. et al., Science, 240:1041-1043, 1988) can be used in the cases of using lacZ promoter and araB promoter, respectively.

As the signal sequence for the secretion of antibody, pelB signal sequence (Lei, S. P. et al., Bacteriol., 169:4379-4383, 1987) can be used in the case of the production in periplasm of *E. coli*. The antibody produced in the periplasm is isolated, and subsequently used by appropriately refolding the antibody structure (see, for example, WO 96/30394).

Those derived from SV40, polyoma virus, adenovirus, bovine papilloma virus (BPV) can be used as a replication origin. Additionally, for the amplification of gene copy number in the host cell system, the expression vector can include aminoglycoside phosphotransferase (APH) gene, thymidine kinase (TK) gene, *E. coli* xanthine guanine phosphoribosyl transferase (Ecogpt) gene, dihydrofolate reductase (dhfr) gene and the like as selection markers.

For the production of the antibody used in the invention, an optional production system can be used. There are in vitro and in vivo systems of the production for making the antibody. The production system in vitro include the production system using eukaryotic cells and the production system using prokaryotic cells.

In the cases of using eukaryotic cells, there are the production systems using animal cells, plant cells, or fungus cells. As the animal cells, (1) mammalian cells, e.g., CHO, COS, myeloma, BHK (baby hamster kidney), HeLa, Vero, etc., (2) amphibian cells, e.g., oocytes of *Xenopus*, or (3) insect cells, e.g., sf9, sf21, Tn5, etc. are known. As plant cells, the cell derived from *Nicotiana tabacum* is known and this can be cultured as callus. As fungus cells, yeast, for example, genus *Saccharomyces*, e.g., *Saccharomyces cerevisiae*, and *Filamentous*, for example, genus *Aspergillus*, e.g., *Aspergillus niger* are known.

In the case of using prokaryotic cells, there are the production systems using bacterial cells. As the bacterial cells, *E. coli* and *Bacillus subtilis* are known.

The antibody can be obtained by introducing the target antibody gene into these cells by transformation and culturing the transformed cells in vitro. The culture is carried out according to the methods known in the art. For instance, DMEM, MEM, RPMI 1640 and IMDM can be used as the medium, and the serum supplement such as fetal calf serum (FCS) can be also combined. The antibody may be produced in vivo by transferring the cells in which the antibody gene is introduced into a peritoneal cavity of the animal.

On the other hand, the production systems in vivo include the production systems using animals and the production systems using plant cells. In the case of using animal cells, there are the production system using mammalian animals and insects.

As the mammalian animals, a goat, swine, sheep, mouse, cattle and the like can be used (Vicki Glaser, Spectrum Biotechnology Applications, 1993). Also, as insects, a silk worm can be used. In the case of using plants, for example, tobacco can be used.

The antibody gene is introduced into these animals or plants, the antibody is produced in the body of the animal or plant, and is collected. For example, the antibody gene is prepared as a fusion gene by inserting in a midstream of the gene encoding the protein inherently produced in milk such as goat β casein. The DNA fragment containing the fusion gene inserted the antibody gene is injected into goat embryo, which is transferred in a female goat. The desired antibody is obtained from the milk of a transgenic goat born from the goat which received the embryo or progenies thereof. Appropriate hormones may be used for the transgenic goat in order to increase an amount of the milk containing the desired antibody (Ebert, K. M. et al., Bio/Technology, 12:699-702, 1994).

In the case of using silk worms, the silk worms are infected with baculovirus inserted the target antibody gene, and the desired antibody is obtained from body fluid of these silk worms (Maeda, S. et al., Nature, 315:592-594, 1985). Moreover, in the case of using tobacco, the target antibody gene is inserted into plant expression vector, e.g., pMON 530, and this vector is introduced into bacteria such as *Agrobacterium tumefaciens*. The tobacco, such as *Nicotiana tabacum*, is infected with these bacteria, and the desired antibody is obtained from leaves of this tobacco (Julian, K. C., Ma, et al., Eur. J. Immunol., 24:131-138, 1994).

When the antibody is produced in the production system in vitro or in vivo as described above, the DNA encoding the antibody heavy chain (H chain) or light chain (L chain) may be separately incorporated into the expression vectors, which may simultaneously transform the host, or the DNA encoding the H chain and L chain are incorporated into a single expression vector, which may transform the host (see International Patent Application Publication No. WO 94-11523).

The antibody used in the invention may be fragments of the antibody or modification thereof as long as the antibody is suitably used. For instance, the fragments of the antibody include, for example, Fab, F(ab')$_2$, Fv, or single chain Fv (scFv) where Fv of the H and L chains are linked by an appropriate linker.

Specifically, the antibody is treated with enzyme, such as papain, pepsin, to generate the antibody fragments, or the gene encoding the antibody fragment is constructed, and this is introduced into the expression vector, which is expressed in an appropriate host cells (see, for example, Co, M. S. et al., J. Immunol., 152:2968-2976, 1994; Better, M. & Horwitz, A.

E., Methods in Enzymology, 178:476-496, 1989; Plueckthun, A. & Skerra, A., methods in Enzymology, 178:476-496, 1989; Lamoyi, E., Methods in Enzymology, 121:652-663, 1989; Rousseaux, J. et al., Methods in Enzymology, 121:663-66, 1989; Bird, R. E. et al., TIBTECH, 9:132-137, 1991).

By ligating the H chain V region to the L chain V region, scFv is obtained. In this scFv, the H chain V region and the L chain V region are preferably linked via a linker, preferably a peptide linker (Huston, J. S. et al., Proc. Natl. Acad. Sci. USA, 85:5879-5883, 1988). The H chain V region and the L chain V region in scFv may de derived from any of those described as the above antibody. As the peptide linker which links the V regions, used is, for example, a given single chain peptide composed of 12 to 19 amino acid residues.

DNA encoding scFv is obtained by amplifying the DNA portion encoding the desired amino acid sequence among DNA encoding the H chain or H chain V region and L chain or L chain V region of the above antibody, which are used as templates using primers which define the both ends thereof by PCR method, then further by amplifying DNA encoding the peptide linker portion and the both ends thereof combining a pair of primers which define to be linked to the H and L chains.

Also, once the DNA encoding scFv is made, the expression vector containing them, and the host transformed with the expression vector can be obtained according to the standard methods, and scFv can be obtained using the host according to the standard methods.

For these antibody fragments, their genes can be obtained, expressed and produced by the hosts as with the above. "Antibody" referred to in the invention includes these antibody fragments.

As modification of the antibody, it is also possible to use the antibody bound to various molecules such as polyethyleneglycol (PEG). "Antibody" referred to in the invention includes these antibody modification. In order to obtain such antibody modifications, they can be obtained by giving chemical modification to the obtained antibody. These methods have been already established in this field.

The antibody produced and expressed as the above can be isolated from inside and outside of cells and the host, and purified to be homogenous. The isolation and purification of the antibody used in the invention can be carried out by affinity chromatography. The column used in the affinity chromatography includes, for example, protein A column and protein G column. Carriers used for the protein A column include Hyper D, POROS, Sepharose F. F. and the like. The other isolation/purification methods used for normal proteins can be used, and the methods are not limited at all.

For example, the antibody used in the invention can be isolated and purified by appropriately selecting and combining chromatography other than the above affinity chromatography, filter, ultrafiltration, salting out, dialysis and so on. Examples of chromatography include ion exchange chromatography, hydrophobic chromatography, gel filtration and the like. Such chromatography can be applied for HPLC (high performance liquid chromatography). Also reverse phase HPLC may be used.

Measurement of concentrations of the antibody obtained above can be carried out by the measurement of absorbance or by ELISA. That is, in the case of the measurement of the absorbance, the antibody is appropriately diluted with PBS (−) followed by measuring the absorbance at 280 nm, and the concentration is calculated by 1 mg/ml as 1.35 OD. In the case by ELISA, the measurement can be carried out as follows. That is, 100 μl of goat anti-human IgG (supplied from TAG) diluted at 1 μg/ml with 0.1 M bicarbonate buffer (pH 9.6) is added to a 96-well plate (supplied from Nunc), and is incubated overnight at 4° C. to immobilize the antibody. After blocking, 100 μl of the appropriately diluted antibody used in the invention or a sample containing the antibody, or human IgG (supplied from Cappel) as the standard is added, and incubated at room temperature for one hour.

After washing, 100 μl of alkaline phosphatase labeled anti-human IgG (supplied from Bio Source) diluted at 5000 folds is added and incubated at room temperature for one hour. After washing, a substrate solution is added followed by the incubation, and subsequently, the absorbance at 405 nm is measured using Microplate Reader Model 3550 (supplied from Bio-Rad) to calculate the concentration of the target antibody.

Modified IL-6 used in the invention is substances having binding activity to IL-6 receptor and which do not transmit the biological activity of IL-6. That is, since the modified IL-6 does not transmit the biological activity of IL-6 although it binds to IL-6 receptor competitively with IL-6, it blocks signal transduction by IL-6.

The modified IL-6 is made by introducing variants by substituting amino acid residues in the amino acid sequence of IL-6. IL-6 which is a source of the modified IL-6 can be obtained from any origin, but it is preferably human IL-6 in consideration of its antigenicity.

Specifically, the modification of IL-6 is carried out by forecasting its secondary structure of IL-6 amino acid sequence using the molecular modeling program known in the art, e.g., WHATIF (Vriend et al., Mol. Graphics, 8:52-56, 1990) and further by evaluating effects of amino acid residues to be substituted on the whole protein. After determining suitable amino acid residues to be substituted, the gene encoding the modified IL-6 is obtained by introducing the variants by the conventional PCR method such that the amino acids are substituted using the vector containing the base sequence encoding human IL-6 gene as the template. The modified IL-6 can be obtained by incorporating this into the appropriate vector as needed and following to the above methods for the expression, production and purification of the recombinant antibody.

Specific examples of the modified IL-6 are disclosed in Brakenhoff et al., J. Biol. Chem., 269:86-93, 1994 and Savino et al., EMBO J., 13:1357-1367, 1994, WO 96/18648 and WO 96/17869.

Partial peptides of IL-6 or partial peptides of IL-6 receptor used in the invention have binding activity to IL-6 receptor or IL-6, respectively, and are substances which do not transmit the biological activity of IL-6. That is, the partial peptide of IL-6 or the partial peptide of IL-6 receptor specifically inhibits the binding of IL-6 to IL-6 receptor by binding to and capturing IL-6 receptor or IL-6, respectively. Consequently, since they do not transmit the biological activity of IL-6, they block the signal transduction by IL-6.

The partial peptide of IL-6 or the partial peptide of IL-6 receptor is the peptide composed of partial or entire amino acid sequence involved in the binding of IL-6 to IL-6 receptor in the amino acid sequence of IL-6 or IL-6 receptor. Such a peptide is composed of typically from 10 to 80, preferably from 20 to 50, and more preferably from 20 to 40 amino acid residues. The partial peptide of IL-6 or the partial peptide of IL-6 receptor can be made by defining the region involved in the binding to IL-6 or IL-6 receptor in the amino acid sequence of IL-6 or IL-6 receptor and synthesizing its partial or entire amino acid sequence by the methods commonly known, e.g., gene engineering technique or peptide synthesis methods.

In order to make the partial peptide of IL-6 or the partial peptide of IL-6 receptor by the gene engineering technique, it can be obtained by inserting the DNA sequence encoding the desired peptide into the expression vector and following to the above expression, production and purification methods of the recombinant antibody.

In order to prepare the partial peptide of IL-6 or the partial peptide of IL-6 receptor by the peptide synthesis method, it is possible to use the methods typically used in peptide synthesis, for example, the solid phase synthesis method or liquid phase synthesis method.

Specifically, the synthesis can be carried out according to Zoku Iyakuhin, Kaihatu Vol. 14 Peptide Gosei, (Ed., Yajima, H., Hirokawa Shoten, 1991). As the solid phase synthesis method, used is, for example, the method where the peptide chain is extended by binding an amino acid corresponding to the C terminus of the peptide to be synthesized to a support which is insoluble in an organic solvent, and alternately repeating a reaction in which one amino acid is sequentially condensed in the direction from the C to N terminus in amino acids of which α-amino group and side chain functional groups are protected with appropriate protecting groups and a reaction in which the protecting group of α-amino group is eliminated in the amino acids or peptide attached on the resin. The solid phase synthesis methods are broadly classified into Boc method and Fmoc method depending on the types of protecting groups used.

After the target peptide is synthesized in this way, deprotection reaction and cleavage reaction of the peptide chain from the support are carried out. In the cleavage reaction of the peptide chain, hydrogen fluoride or trifluoromethane sulfonate and TFA can be typically used in Boc method and Fmoc method, respectively. In Boc method, the above protected peptide resin is treated with hydrogen fluoride in the presence of anisole. Then, the elimination of the protecting group and the cleavage from the support are carried out to recover the peptide. This is lyophilized to yield the crude peptide. On the other hand, in Fmoc method, for example, in TFA, the deprotection reaction and the cleavage reaction of the peptide chain from the support can be carried out by the same manipulation as the above.

The resultant crude peptide can be isolated and purified by applying on HPLC. The elution can be performed under an optimal condition using a water-acetonitrile solvent typically used for the purification of protein. Fractions corresponding to peaks in a profile of the resultant chromatography are collected and lyophilized. The peptide fractions purified in this way are identified by analysis of molecular weights by mass spectrometry, amino acid composition analysis or amino acid sequence analysis.

The specific examples of the partial peptides of IL-6 and IL-6 receptor are disclosed in JP-A-2-188600, 7-324097, and 8-311098, and U.S. Pat. No. 5,210,075.

The pharmaceutical compositions of the invention may be those containing pharmaceutically acceptable carriers and additives depending on their administration pathways. Examples of such carriers and additives include water, pharmaceutically acceptable organic solvents, collagen, polyvinyl alcohol, polyvinylpyrrolidone, carboxyvinyl polymer, sodium carboxymethylcellulose, sodium polyacrylate, sodium arginate, water-soluble dextran, sodium carboxymethyl starch, pectin, methyl cellulose, ethyl cellulose, xanthane gum, gum arabic, casein, gelatin, agarose, diglycerin, propyleneglycol, polyethylene glycol, petrolatum, paraffin, stearyl alcohol, stearic acid, human serum albumin (HSA), mannitol, sorbitol, lactose, acceptable surfactants as pharmaceutical additives and the like. The additives used are selected appropriately from the above or in combination depending on their formulation, but are not limited thereto.

EXAMPLES

The present invention is specifically described below by examples and reference examples, but the invention is not limited thereto.

Example 1

MRA is a recombinant humanised anti-human interleukin-6 receptor monoclonal antibody of the IgG1 sub-class that inhibits the function of the cytokine interleukin-6 (IL-6). In early studies in Japan and Europe, MRA showed promise in the treatment of rheumatoid arthritis and was tolerated well.

This was a large, Phase II trial of MRA to determine the optimum dose of MRA given alone and in combination with methotrexate for the treatment of rheumatoid arthritis. The potential efficacy of repeated intravenous doses of MRA, both as monotherapy and in combination with methotrexate, were assessed in patients with active rheumatoid arthritis despite of the treatment with methotrexate for a specified period of time and compared to methotrexate monotherapy. The efficacy, safety and tolerability of MRA were assessed.

Methods:

Subjects: Patients with rheumatoid arthritis diagnosed based on the 1987 disease classification of the American College of Rheumatology (ACR), of at least 6 months duration were enrolled. Patient must have active disease and had an inadequate response to, or disease flare on MTX given for at least 6 months at a dose of at least 12.5 mg weekly or 10 mg weekly in the case of intolerance.

Study design: a double-blind, randomized, parallel group study by central randomization method Dosage and Administration: Seven groups: 0 mg/kg (placebo)+MTX, 2 mg/kg MRA+MTX, 4 mg/kg MRA+MTX, 8 mg/kg MRA+MTX, 2 mg/kg MRA+MTX placebo, 4 mg/kg MRA+MTX placebo, and 8 mg/kg MRA+MTX placebo. MRA or placebo administration is given by intravenous infusion, at 4-week intervals. MTX or MTX placebo administration is given orally, once weekly, at 10-25 mg/week.

Study Method: The assigned dose was administered by intravenous infusion, four times in total at 4-week intervals, and efficacy and safety were evaluated at 2-week intervals up to 16 weeks, and follow-up observation was done at 20 weeks. The primary endpoint for efficacy was the rate of ACR 20 at 16 weeks (4 weeks after the last dose). Secondary endpoints included rates of ACR 50 and ACR 70 at 16 weeks (4 weeks after the last dose).

ACR improvement criteria: The cases where among the following 7 items, the number of swelling joints and the number of pain joints are improved by 20% or more and improvement by 20% or more is observed in three out of the remaining five items are determined as 20% or more improvement in ACR criteria. Further, 50% and 70% improvement cases indicate the patient cases where the above 20% improved parts are improved by 50% and 70%, respectively.

(1) Number of swelling joints
(2) Number of tender joints
(3) Pain assessment by a patient
(4) Global assessment of disease activity by a patient
(5) Global disease activity by a physician
(6) Assessment of physical function by a patient
(7) CRP or ESR

TABLE 1

|        | 2 mg/kg MRA | 4 mg/kg MRA | 8 mg/kg MRA | MTX |
|--------|-------------|-------------|-------------|------|
| ACR 20 | 30.8%       | 61.1%       | 62.7%       | 40.8% |
| ACR 50 | 5.8%        | 27.8%       | 41.2%       | 28.6% |
| ACR 70 | 1.9%        | 5.6%        | 15.7%       | 16.3% |

|        | 2 mg/kg MRA + MTX | 4 mg/kg MRA + MTX | 8 mg/kg MRA + MTX |
|--------|-------------------|-------------------|-------------------|
| ACR 20 | 64.0%             | 63.3%             | 73.5%             |
| ACR 50 | 32.0%             | 36.7%             | 53.1%             |
| ACR 70 | 14.0%             | 12.2%             | 36.7%             |

Statistically significantly higher ACR 20 improvement rate was observed in all groups except the MRA alone 2 mg/kg group compared to the control group. In the MRA 8 mg/kg+MTX group, ACR 50 and 70 improvement rate were 53.1% and 36.7%, respectively, which were statistically significantly higher than those of the control group which were 28.6% and 16.3%, respectively. In the MRA alone groups, statistically significant dose dependency was observed in ACR 20 improvement rate. Also, for ACR50 and ACR70 improvement rate, the statistically significant dose dependent response was observed in both MRA alone and MTX-combined groups.

Reduction of Swollen Joint Count (Table 2)

The mean swollen joint count was similar across all the treatment groups at baseline.

There was a cumulative reduction in the mean swollen joint count from baseline with increasing duration of exposure in all seven treatment groups. The mean reduction in the swollen joint count in the MRA 8 mg/kg group was statistically significant compared with the reduction in the MTX group (p=0.010). At Week 16, the mean difference (95% CI) between the MRA 8 mg/kg group and the MTX group was −2.31 (−4.07, −0.55). There was a statistically significant linear dose-relationship between the MRA monotherapy groups (p<0.001). The mean reduction in swollen joint count in the MRA 8 mg/kg+MTX group was statistically significant compared with the reduction in the MTX group (p<0.001). The mean difference (95% CI) between the MRA 8 mg/kg+MTX group and the MTX group was −3.62 (−5.39, −1.84). There was a statistically significant linear dose-relationship between the MRA combination therapy groups (p=0.004).

TABLE 2

|  | 2 mg/kg MRA | 4 mg/kg MRA | 8 mg/kg MRA | MTX |
|---|---|---|---|---|
| Baseline: | | | | |
| N | 52 | 54 | 51 | 49 |
| Mean ± SD | 11.6 ± 4.6 | 11.1 ± 4.4 | 12.2 ± 5.2 | 12.7 ± 4.2 |
| Change from Baseline: | | | | |
| Week 16 N | 42 | 43 | 43 | 39 |
| Mean ± SD | −4.5 ± 5.7 | −5.8 ± 4.1 | −8.4 ± 4.6 | −5.7 ± 6.1 |

|  | 2 mg/kg MRA + MTX | 4 mg/kg MRA + MTX | 8 mg/kg MRA + MTX |
|---|---|---|---|
| Baseline: | | | |
| N | 50 | 49 | 49 |
| Mean ± SD | 11.9 ± 4.3 | 11.9 ± 3.9 | 11.8 ± 3.9 |
| Change from Baseline: | | | |
| Week 16 N | 46 | 42 | 44 |
| Mean ± SD | −6.2 ± 4.6 | −6.8 ± 5.4 | −9.4 ± 4.0 |

Among 359 enrolled patients, the safety evaluation sets, the full analysis sets, and PPS (per protocol set) were 359, 354, and 307, respectively. Total 359 patients were enrolled, 299 completed the study, and the 60 were withdrawn. Among the withdrawn patients, 33 were due to adverse events, one was due to complication with the other disease, seven were due to adverse events, 7 were due to the use of drugs with prohibited concomitant use, five were due to withdrawal of informed consent, one was due to lost to follow up, and 22 were due to lack of efficacy (including multiple reasons).

Among serious adverse events of which causal relationship could not be denied, five cases of infection were reported. That is, one patient with foot abscess and osteomyelitis in the 2 mg/kg MRA group, one patient with chest infection and pleurisy, one patient with septicaemia in the 8 mg/kg MRA+MTX group, one patient with septicaemia in the 8 mg/kg MRA+MTX group, and one patient with joint infection in the 8 mg/kg MRA+MTX group, were reported. In addition to them, five cases of hypersensitivity were reported as serious adverse events of which causal relationship could not be denied that is, four patients of hypersensitivity in the 2 mg/kg MRA group and one patient of hypersensitivity in the 4 mg/kg MRA group were reported. All of these events of hypersensitivity occurred in no combination with MTX after the 3rd or 4th MRA administration.

Concerning the laboratory data values for hepatic functions, although the elevation of ALT and AST levels were observed as a result of MRA use, such elevations were equivalent to those observed in the other patients with rheumatoid arthritis. The increase of the laboratory data relating to lipids (total cholesterol, HDL cholesterol and triglyceride) was observed in the MRA groups. However, there was no overall change in Atherogenic Index.

Slight transient decrease of neutrophil count occurred in some patients. The clinically significant changes of the parameters for disease activity, i.e., the decreases of CRP and ESR and the elevation of hemoglobin were observed in a dose dependent manner.

Infusion Reaction

An infusion reaction was defined as an adverse event occurring within 24 hours of study drug administration. The number of patients experiencing an infusion reaction in each treatment group suggested a possible inverse dose-response for MRA.

Anti-MRA Antibody

The development of anti-MRA antibodies was examined. None occurred at the 8 mg/kg treatment groups (monotherapy or combination with MTX). At 2 or 4 mg/kg treatment groups, the number of incidents was less in groups in combination with MTX than MRA monotherapy groups.

Results

A clear dose-response was observed for MRA monotherapy and for MRA combined with methotrexate. The effectiveness of MRA to treat patients with rheumatoid arthritis was confirmed for both MRA monotherapy and for MRA combined with methotrexate. Also, safety of MRA was confirmed in both MRA monotherapy and for MRA combined with methotrexate.

Reference Example 1

Preparation of Human Soluble IL-6 Receptor

The soluble IL-6 receptor was made by the PCR method using plasmid, pBSF2R.236 containing cDNA encoding IL-6 receptor obtained according to Yamasaki et al's method (Yamasaki, K. et al., Science, 241:825-828, 1988). The plasmid, pBSF2R.236 was digested with a restriction enzyme, Sph1 to obtain IL-6 receptor cDNA, which was then inserted into mp18 (supplied from Amersham). Variants were introduced into the IL-6 receptor cDNA in PCR method by in vitro mutagenesis system (supplied from Amersham) using synthetic oligoprimers designed to introduce a stop codon into the cDNA of IL-6 receptor. This manipulation introduced the stop codon at position 345 of the amino acid to give the cDNA encoding the soluble IL-6 receptor.

The soluble IL-6 receptor cDNA was ligated to the plasmid pSV (supplied from Pharmacia) to afford the plasmid pSVL344 in order to express the cDNA in CHO cells. The soluble IL-6 receptor cDNA digested with HindIII-SalI was inserted into the plasmid pECEdhfr containing cDNA of dhfr to give CHO cell expression plasmid pECEdhfr344.

By the calcium phosphate precipitation method (Chen, C. et al., Mol. Cell. Biol., 7:2745-2751, 1987), 10 µg of the plasmid pECEdhfr344 was transfected into dhfr-CHO cell line DXB-11 (Urlaub, G. et al., Proc. Natl. Acad. Sci. USA, 77:4216-4220, 1980). The transfected CHO cells were cultured for 3 weeks in αMEM selection medium containing 1 mM of glutamine, 10% of dialyzed FCS, 100 U/ml of penicillin and 100 µg/ml of streptomycin without nucleoside.

The selected CHO cells were screened by the limiting dilution method, and a single clone of CHO cells was obtained. This CHO clone was amplified with methotrexate at the concentration of 20 nM to 200 nM to obtain CHO cell line 5E27 which produces the human soluble IL-6 receptor. CHO cell line 5E27 was cultured in Iscove's modified Dulbecco medium (IMDM, supplied from Gibco) containing 5% FBS. The culture supernatant was collected, and the concentration of the soluble IL-6 receptor in the culture supernatant was measured by ELISA. As a result, it was affirmed that the soluble IL-6 receptor was present in the culture supernatant.

Reference Example 2

Preparation of Anti-Human IL-6 Antibody

BALB/c mouse was immunized with 10 µg of recombinant IL-6 (Hirano, T. et al., Immunol. Lett., 17:41, 1988) along with Freund's complete adjuvant, and the immunization was continued every one week until anti-IL-6 antibody was detected in serum. Immunized cells were removed from local lymph nodes and fused with myeloma cell line, P3U1 using polyethyleneglycol 1500. Hybridomas were selected according to Oi et al's method (Selective Methods in Cellular Immunology, W. H. Freeman and Co., San Francisco, 351, 1980) using HAT medium, and the hybridoma producing anti-human IL-6 antibody was established.

IL-6 binding assay was carried out as follows for the hybridomas producing anti-human IL-6 antibody. That is, a flexible polyvinyl 96-well microplate (supplied by Dynatech Laboratories, Inc., Alexandra, Va.) was coated with 100 µl of goat anti-mouse Ig (10 µl/ml; supplied from Cooper Biomedical Inc., Malvern, Pa.) in 0.1 M carbonate-hydrogen carbonate buffer (pH 9.6) at 4° C. overnight. Then, the plate was treated with 100 µl of PBS containing 1% of bovine serum albumin (BSA) for 2 hours at room temperature.

This was washed with PBS, subsequently 100 µl of the hybridoma culture supernatant was added to each well, and incubated at 4° C. overnight. The plate was washed, then $^{125}$I labeled recombinant IL-6 was added to each well to be at 2000 cpm/0.5 ng/well, the plate was washed, and subsequently radioactivity in each well was measured by a gamma counter (Beckman Gamma 9000, Beckman Instruments, Fullerton, Calif.). Consequently, 32 out of 216 hybridoma clones were positive in the IL-6 binding assay. Among these clones, finally stable MH166.BSF2 was obtained. The anti-IL-6 antibody MH166 produced by the hybridoma has a subtype of IgG1κ.

Then, neutralization activity of MH166 antibody for the growth of hybridomas was examined using IL-6 dependent mouse hybridoma clone MH60.BSF2. MH60.BSF2 cells were dispensed at 1×10$^4$/200 µl/well, a sample containing MH166 antibody was added thereto followed by being cultured for 48 hours, and 0.5 µCi/well of $^3$H thymidine (New England Nuclear, Boston, Mass.) was added. After an additional 6 hours culture, the cells were placed on glass filter paper, and treated using an automatic harvester (Labo Mash Science Co., Tokyo, Japan). Rabbit anti-IL-6 antibody was used as the control.

As a result, MH166 antibody inhibited $^3$H thymidine uptake of MH60.BSF2 cells induced by IL-6 in a dose dependent manner. This demonstrated that MH166 antibody neutralized the activity of IL-6.

Reference Example 3

Preparation of Anti-Human IL-6 Receptor Antibody

Anti-IL-6 receptor antibody MT18 made by Hirano et al's method (Hirano, Y. et al., J. Immunol., 143:2900-2906, 1989) was bound to Sepharose 4B (supplied from Pharmacia Fine Chemicals; Piscataway, N.J.) activated by CNBr according to the attached formulation to purify IL-6 receptor (Yamasaki, K. et al., Science, 241:825-828, 1988). Human myeloma cell line, U266 cells were solubilized with 1 mM of p-para-aminophenylmethane sulfonylfluoride hydrochloride (supplied from Wako Chemicals) containing 1% of digitonin (supplied from Wako Chemicals), 10 mM of ethanolamine (pH 7.8) and 1.5 M of NaCl (digitonin buffer), and mixed with MT18 antibody bound to Sepharose 4B beads. Subsequently, the beads were washed with the digitonin buffer six times, and rendered as partially purified IL-6 receptor for immunization.

BALB/c mouse was immunized with the above partially purified IL-6 receptor obtained from 3×10$^9$ U266 cells every 10 days four times, and subsequently hybridomas were made by the standard method. Binding activity to IL-6 receptor was examined in the hybridoma culture supernatants from growth positive wells by the following method. U266 cells at 5×10$^7$ were labeled with $^{35}$S-methionine (2.5 mCi), and solubilized with the above digitonin buffer. The solubilized U266 cells were mixed with 0.04 ml volume of MT18 antibody bound to Sepharose 4B beads, subsequently washed with the digitonin buffer six times, then $^{35}$S-methionine labeled IL-6 receptor was eluted with 0.25 ml of the digitonin buffer (pH 3.4), and neutralized with 0.025 ml of 1M Tris (pH 7.4).

The hybridoma culture supernatant (0.05 ml) was mixed with 0.01 ml of Protein G Sepharose (supplied from Pharmacia). After washing, the Sepharose was incubated with 0.005 ml of the $^{35}$S-methionine labeled IL-6 receptor solution prepared above. Immunoprecipitate was analyzed by SDS-PAGE, and the hybridoma culture supernatants which reacted with IL-6 receptor were examined. Consequently, a reaction positive hybridoma clone, PM-1 (FERM BP-2998) was established. The antibody produced by the hybridoma, PM-1 has a subtype of IgGκ.

Inhibitory activity of the antibody produced by the hybridoma PM-1 was examined for the binding of IL-6 to human IL-6 receptor using the human myeloma cell line, U266. The human recombinant IL-6 was prepared from *E. coli* (Hirano, T. et al., Immunol. Lett., 17:41-45, 1988), and $^{125}$I-labeled (Taga, T. et al., J. Exp. Med., 166:967-981, 1987) by Bolton-Hunter reagent (New England Nuclear, Boston, Mass.).

U266 cells at $4 \times 10^5$ were cultured with 70% (v/v) of the hybridoma PM-1 culture supernatant and 14000 cpm of $^{125}$I-labeled IL-6. A sample (70 μl) was layered on 300 μl of FCS in a 400 μl microfuge polyethylene tube, and centrifuged followed by measuring radioactivity on the cells.

Consequently, the antibody produced by the hybridoma PM-1 was demonstrated to inhibit the binding of IL-6 to IL-6 receptor.

Reference Example 4

Preparation of Anti-Mouse IL-6 Receptor Antibody

A monoclonal antibody against mouse IL-6 receptor was prepared by the method described in Saito, T. et al., J. Immunol., 147:168-173, 1991.

CHO cells which produce mouse soluble IL-6 receptor were cultured in IMDM medium containing 10% FCS, and the mouse soluble IL-6 receptor was purified from the culture supernatant using an affinity column where the anti-mouse IL-6 receptor antibody RS12 (See the above Saito, T. et al.) was fixed onto Affigel 10 gel (supplied from Biorad).

The resultant mouse soluble IL-6 receptor (50 μg) was mixed with Freund's complete adjuvant, which was injected into peritoneal cavity of a Wistar rat. After two weeks, additional immunization was started with Freund's incomplete adjuvant. On the 45th day, spleen cells of the rat were removed, and $2 \times 10^8$ cells were fused with $1 \times 10^7$ mouse myeloma P3U1 cells by the standard method using 50% of PEG1500 (supplied from Boehringer Mannheim) followed by screening hybridomas in HAT medium.

The hybridoma culture supernatants were added to a plate coated with rabbit anti-rat IgG antibody (supplied from Cappel), and subsequently the mouse soluble IL-6 receptor was reacted. Then, the hybridomas producing the antibody against the mouse soluble IL-6 receptor were screened by ELISA method using rabbit anti-mouse IL-6 receptor antibody and alkaline phosphatase labeled sheep anti-rabbit IgG. The hybridoma clone in which the production of the antibody was affirmed was subcloned twice, and a single hybridoma clone was obtained. This clone was named MR16-1.

Neutralization activity of the antibody produced by this hybridoma was examined for signal transduction of mouse IL-6 by uptake of $^3$H thymidine using MH60.BSF2 cells (Matsuda, T. et al., J. Immunol., 18:951-956, 1988). MH60.BSF2 cells were prepared to be $1 \times 10^4$ cells/200 μl/well in a 96-well plate. To this plate, 10 pg/ml of mouse IL-6 and 12.3 to 1000 ng/ml of MR16-1 antibody or RS12 antibody were added, then cultured at 37° C. for 44 hours at 5% $CO_2$, and subsequently 1 μCi/well of $^3$H thymidine was added. 4 hours later, the uptake of $^3$H thymidine was measured. Consequently, MR16-1 antibody suppressed uptake of $^3$H thymidine of MH60.BSF2 cells.

Accordingly, the antibody produced by the hybridoma MR16-1 (FERM BP-5875) was demonstrated to inhibit the binding of IL-6 to IL-6 receptor.

What is claimed is:

1. A method for treating rheumatoid arthritis, comprising administering an effective amount of an interleukin-6 (IL-6) antagonist and an effective amount of methotrexate (MTX) to a patient in need thereof, wherein the IL-6 antagonist is an anti-IL-6 antibody which inhibits binding of IL-6 to the IL-6 receptor by binding IL-6 and blocks signal transduction by IL-6.

2. The method according to claim 1, wherein the IL-6 is a human IL-6 and the IL-6 receptor is a human IL-6 receptor.

3. The method of claim 1, wherein the anti-IL-6 antibody is the MH166 antibody.

4. The method according to claim 1, wherein the amount of the anti-IL-6 antibody administered is 0.02 to 150 mg/kg/4 weeks and the amount of MTX administered is 1 to 100 mg/kg/week.

5. The method according to claim 1, wherein the anti-IL-6 antibody and MTX are administered simultaneously.

6. The method according to claim 1, wherein the anti-IL-6 antibody and MTX are administered at different times.

7. The method according to claim 1, wherein the anti-IL-6 antibody is administered by intravenous injection.

* * * * *